(12) United States Patent
Meyer et al.

(10) Patent No.: US 11,583,474 B2
(45) Date of Patent: Feb. 21, 2023

(54) FEEDING, TEETHING, AND/OR ENTERTAINING DEVICE

(71) Applicant: The Clever Baby, LLC, Chicago, IL (US)

(72) Inventors: Tricia L. Meyer, Lemont, IL (US); Michael J. Meyer, Lemont, IL (US)

(73) Assignee: THE CLEVER BABY, LLC, Chicago, IL (US)

( * ) Notice: Subject to any disclaimer, the term of this patent is extended or adjusted under 35 U.S.C. 154(b) by 274 days.

(21) Appl. No.: 16/811,836

(22) Filed: Mar. 6, 2020

(65) Prior Publication Data

US 2021/0275399 A1 Sep. 9, 2021

(51) Int. Cl.
*A61J 7/00* (2006.01)
*A61J 17/02* (2006.01)

(52) U.S. Cl.
CPC ............ *A61J 7/0053* (2013.01); *A61J 17/02* (2013.01)

(58) Field of Classification Search
CPC .. A61J 7/0053; A61J 7/00; A61J 17/02; A61J 17/109; A61J 17/113; A61J 17/111; A61J 11/005; A61J 11/0005; A61J 11/00; A61J 11/02; A61J 11/0055; A61J 7/0069; A61J 9/06; A61J 9/0661
See application file for complete search history.

(56) References Cited

U.S. PATENT DOCUMENTS

| | | |
|---|---|---|
| 2,845,065 A | 7/1958 | Gabriel |
| 3,299,891 A | 1/1967 | Smeton |
| 5,871,184 A | 2/1999 | Kaopio |
| 6,523,792 B2 | 2/2003 | Fishler |
| 6,641,094 B2 | 11/2003 | Fishler |
| 6,827,317 B1 * | 12/2004 | Maki Risaliti .......... A61J 17/02 248/105 |
| D612,063 S | 3/2010 | LaPorte |
| D612,492 S | 3/2010 | Krumins |
| D612,938 S | 3/2010 | Grogan |
| D621,450 S | 8/2010 | Wong |
| D621,451 S | 8/2010 | Wong |
| D634,002 S | 3/2011 | Laerdal et al. |
| 8,490,831 B1 | 7/2013 | Wong et al. |
| 9,016,520 B2 | 4/2015 | Orlowski et al. |
| D729,379 S | 5/2015 | Ko |
| D762,298 S | 7/2016 | Ko |
| 9,427,674 B2 | 8/2016 | Di |
| D797,919 S | 9/2017 | Ko |

(Continued)

FOREIGN PATENT DOCUMENTS

| | | |
|---|---|---|
| CZ | 33333 | 10/2019 |
| KR | 200195386 Y1 | 9/2000 |

(Continued)

OTHER PUBLICATIONS

Extended European Search Report for European Application No. EP 21160210.7, dated Aug. 18, 2021 (9 pages).

(Continued)

*Primary Examiner* — Erich G Herbermann
(74) *Attorney, Agent, or Firm* — McCracken & Gillen LLC

(57) ABSTRACT

A device comprises a syringe and a body carrying the syringe and comprising one or more of an action figure, a miniaturized version of a useful article, a fanciful version of a useful article, a playful or fanciful other object, or the like.

11 Claims, 3 Drawing Sheets

(56) References Cited

U.S. PATENT DOCUMENTS

| | | |
|---|---|---|
| D863,551 S | 10/2019 | Kucera |
| 10,427,060 B2 | 10/2019 | Corwin |
| 10,881,586 B1 | 1/2021 | Hafizi |
| 2006/0089077 A1* | 4/2006 | Wittschen ............. A61J 7/0053 446/77 |
| 2013/0331000 A1* | 12/2013 | Drozdowski ............ A63H 3/02 446/369 |
| 2016/0360908 A1 | 12/2016 | Naraine et al. |
| 2019/0030444 A1* | 1/2019 | Corwin .................... F16B 2/22 |

FOREIGN PATENT DOCUMENTS

| | | |
|---|---|---|
| WO | 9426325 A1 | 11/1994 |
| WO | 2021059011 | 4/2021 |

OTHER PUBLICATIONS

Google Translation of Czechoslovakia Patent No. CZ33333U1 (12 pages).

Extended European Examination Report issued in connection with European Patent Appl. No. EP 21160210.7, dated Jul. 19, 2022 (7 pages).

\* cited by examiner

FEEDING, TEETHING, AND/OR ENTERTAINING DEVICE

FIELD OF DISCLOSURE

The present subject matter relates to a device adapted for use for a child, and more particularly to a device for feeding and/or entertaining a child.

BACKGROUND

Feeding a child, particularly an infant or toddler, is often a messy and time consuming task. Typically, when the child is young, a small spoon is used to scoop soft foods out of a jar and the food is given to the child. When the child is very young, the child may not yet be trained to open her or his mouth when the spoon is offered, thereby resulting in multiple attempts to get the child to open her/his mouth so that the food can be deposited therein. Even an older child who knows to open her/his mouth when a spoonful of food is offered may accept only a portion of the food being offered, and spit out the rest. At times, an entire spoonful of food may be lost either on the way to the child or after the child has received the spoonful.

Also, as any parent knows, a child often likes to chew on various items frequently, but not always, because the child is teething or the child is at a particular developmental stage during which the child is particularly aware of her/his mouth. At times, the child may wish to teeth on a feeding spoon or other article, which often is not resilient or soothing to the child.

SUMMARY

According to one aspect, a feeding device comprises a syringe and integral body and comprising one or more of an action figure, a miniaturized version of a useful article, a fanciful version of a useful article, or a playful or fanciful other object. The body includes flexible surfaces defining a recess and a slot wherein the recess and the slot extend along substantially a full length of the body between a front body end a back body end, the slot is in communication with the recess over the full length of the body, and the body includes a reduced diameter flange at one end of the body and an entirety of the body comprises a teething device. Further, the syringe is separate from the body and is removably carried by the body inside the recess in abutment with both the flexible surfaces and the reduced diameter flange and wherein the syringe is exposed outside of the body by the slot over the full length of the body.

According to another aspect, a device comprises a syringe and integral body carrying the syringe and comprising one or more of an action figure, a miniaturized version of a useful article, a fanciful version of a useful article, or a playful or fanciful other object. The body includes a recess extending substantially along the length of the body wherein the syringe is carried in the recess and is separate from the body, the body comprises a flexible outer member extending over an entirety of the body and one or more of a freezable liquid and a freezable gel disposed in the flexible outer member, and the entirety of the body comprises a teething device. In addition, the syringe includes a cylindrical barrel and a surface proximate an end of the syringe having a shoulder and the body includes a cylindrical recess that fixedly receives the barrel and a reduced diameter flange wherein the shoulder abuts the reduced diameter flange.

Other aspects and advantages will become apparent upon consideration of the following detailed description and the attached drawings wherein like numerals designate like structures throughout the specification.

DETAILED DESCRIPTION

Figure 1:
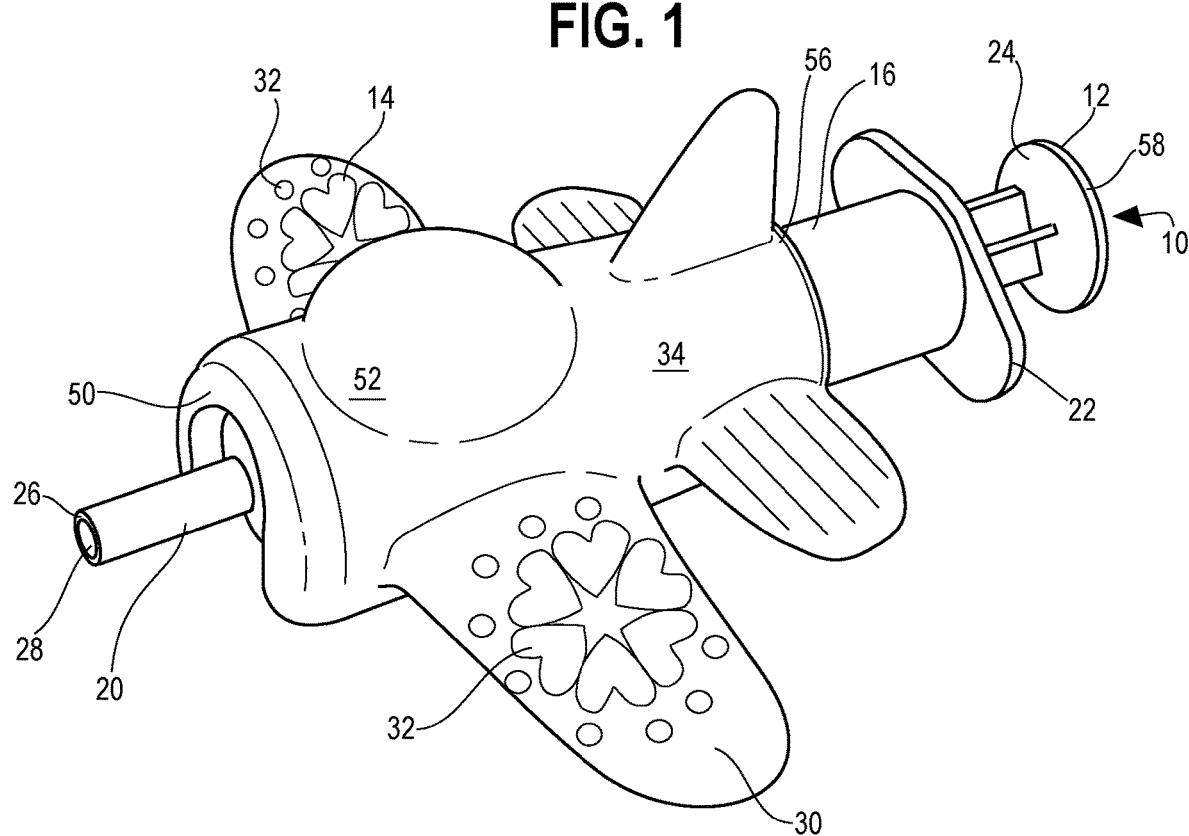
FIGS. 1 and 2 are perspective views of opposite sides of a feeding and/or entertaining device
Figure 2:
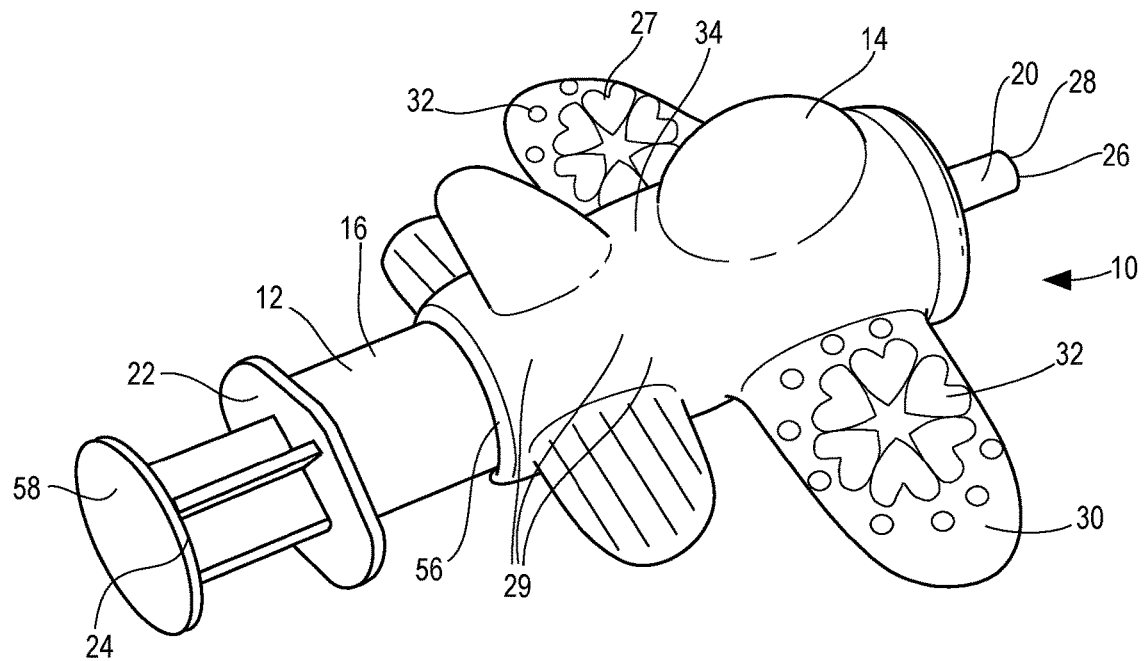
Figure 3:
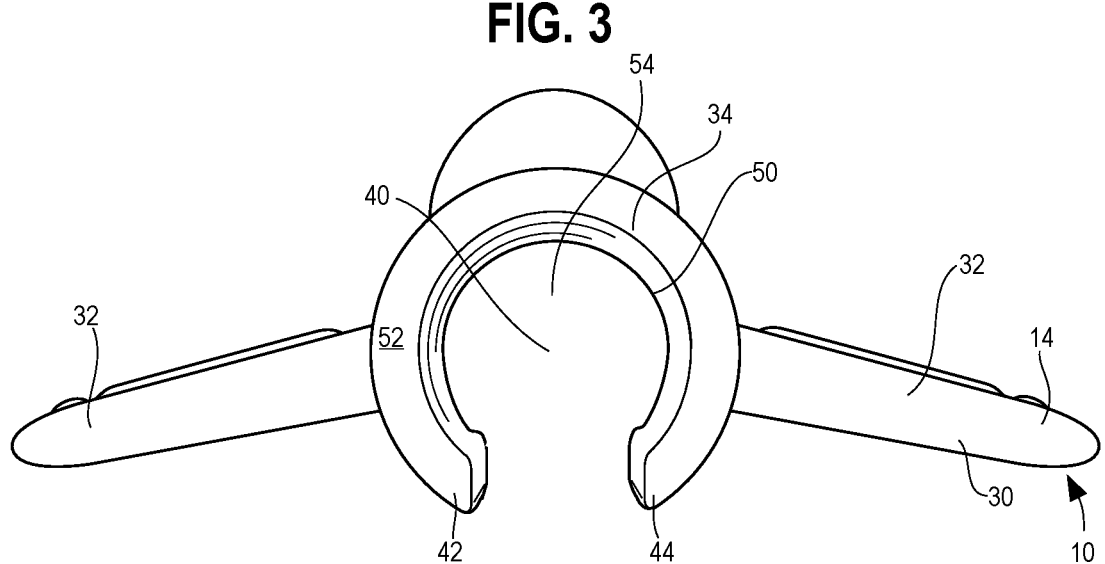
FIG. 3 is a front elevational view of the device of FIGS. 1 and 2.
Figure 4:
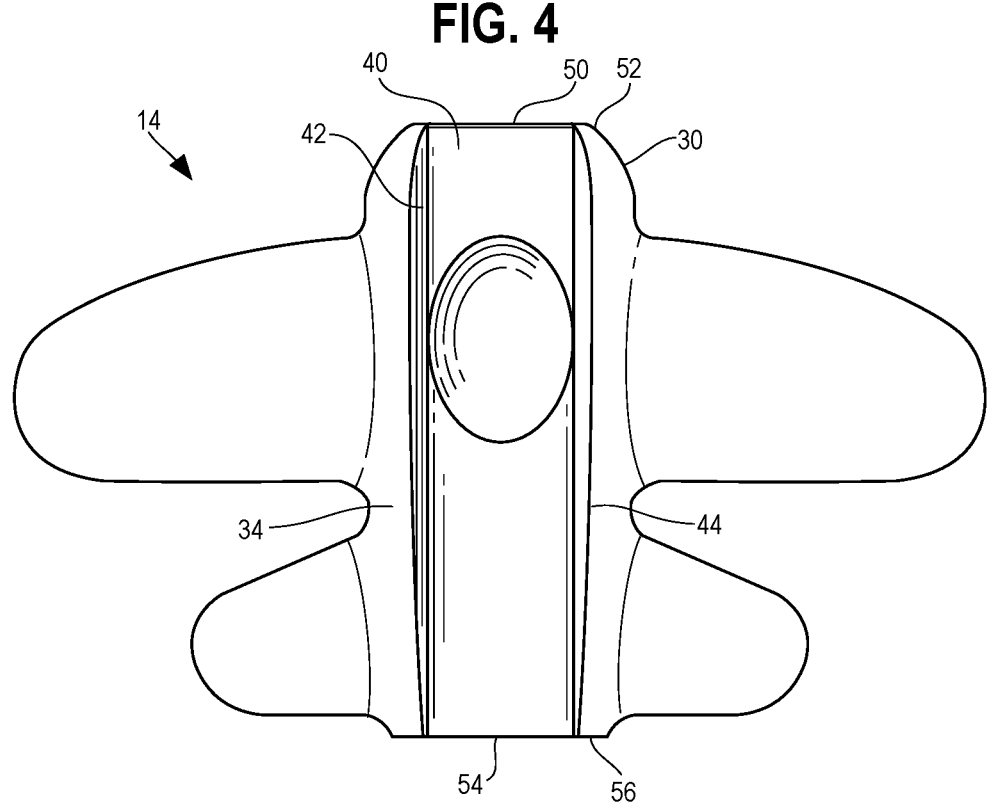
FIG. 4 is a bottom elevational view of the device of FIGS. 1 and 2.
Figure 5:
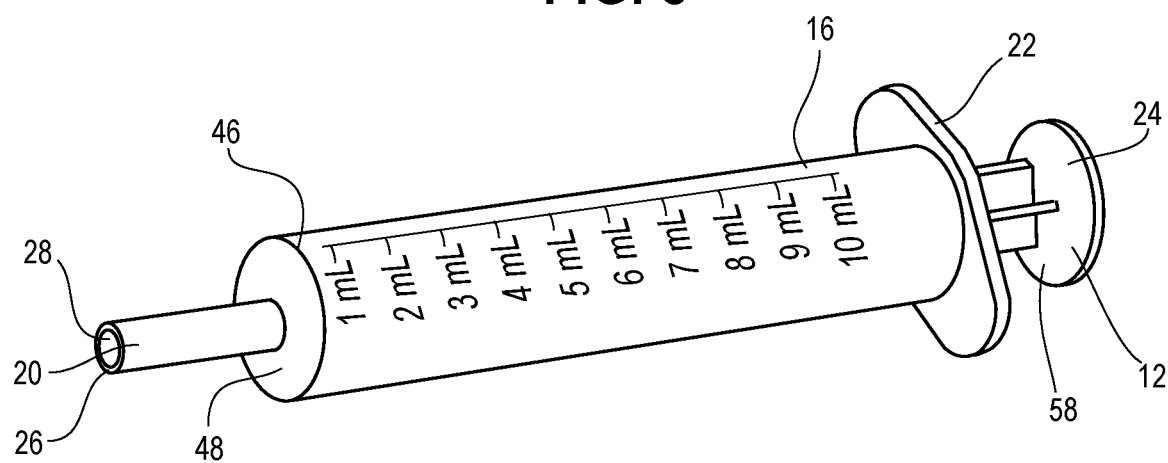
FIG. 5 is an isometric view of the syringe of FIGS. 1 and 2.

FIGS. 1-4 show an embodiment of a feeding, teething, and/or entertaining device 10 comprising a syringe 12 retained within a surrounding structure or body comprising a toy 14, which may comprise a teething device. Referring also to FIG. 5 the syringe 12 comprises a cylindrical barrel 16 having an inlet/outlet end 20 and a plunger end 22. A plunger 24 is disposed in the barrel 16 and is movable therealong, as is conventional. The outlet end 20 has a cylindrical end portion or tip 26 defining an open bore 28.

In the preferred embodiment, the toy 14 comprises a resilient body 30 made of, for example, a food-grade plastic or other flexible material. One or more portions or all of the body 30 may be solid or hollow and, in the latter case, optionally filled with a non-toxic material 27 (FIG. 2), optionally a material 27 having a freezing point near zero degrees Celsius (or thereabouts) so that the material may be chilled to an acceptable temperature and/or frozen in a conventional household refrigerator. Also, the body 30 and the material 27 are preferably capable of being slightly warmed. The material may comprise water with or without a thickening agent to form a gel, or the like. Preferably, the water or gel may or may not have particulate matter 29 (FIG. 2) entrained or dispersed therein, such as metallic sparkle material, confetti-like material, balls or other shaped plastic bodies, etc. that may be visible from outside the toy 14. The body 30 is made of a non-toxic material, preferably BPA-free and free of other non-desirable materials, and preferably capable of flexing to permit expansion and contraction and withstanding bite forces without rupture. If desired, all of the body 30 may be resilient, or only one or more portions may be resilient, such as wings 32 and a fuselage portion 34 of the toy 14, while other portions may be rigid. Some portions of the toy 14 may be separate from other portions, or the toy 14 may be a single integral member. Portions of the toy 14 may be dyed with toxin-free materials that are certified as safe for human consumption.

Also, the toy is readily cleanable, and, more preferably, can be cleaned in a dishwasher. As illustrated, the toy 14 comprises an airplane. More generally, the toy 14 may comprise any action figure, a miniaturized version of a useful article, a fanciful version of a useful article, a playful or fanciful other object, or the like, e.g., a teddy bear, a car, a cartoon character, etc. and combinations thereof.

Also in the preferred embodiment, the syringe 12 is securely retained in a cylindrical or other shaped recess 40 in the toy 14 (best seen in FIGS. 3 and 4) by a press fit with flexible surfaces defining the recess 40. The syringe 12 is inserted into the toy 14 by pressing the barrel 16 upwardly between resilient lower lips 42, 44 in the fuselage portion 34 until the barrel 16 passes the lips 42, 44, whereupon the lips 42, 44 at least substantially return to their original shape, whereupon the barrel, and thus the syringe 12 is retained in the recess. Also, a shoulder 46 of a surface 48 near the inlet/outlet end 20 of the syringe 12 abuts and bears against a reduced diameter flange 50 extending circumferentially about a first end 52 of the toy 14 defining the recess 40. Preferably, the surfaces defining the recess 40 are at least substantially complementary to the shape of the barrel 16 and the remainder of the portions of the syringe 12 that are disposed in the recess 40. Also, it is advantageous to permit the syringe to be readily removable from the recess 40 by reversing the above-noted steps so that the syringe 12 and the toy 14 can be cleaned separately.

If desired, the syringe 12 may be assembled within the recess 40 by inserting the syringe 12 in an opening 54 at a second end 56 opposite the first end 52 and sliding the barrel 16 into the recess 40 axially until the shoulder 46 engages the flange 50. Removing the syringe may also be accomplished by grasping a handle 58 of the syringe 12 and retracting the barrel 16 from the recess 40.

Preferably, the syringe 12 is made of a hard plastic material that is safe to use with foods and liquids, such as liquid medicines. Also, preferably, the syringe 12 has a capacity sufficient to accommodate enough food/liquid so the excessive refilling is avoided. Still further, the bore 28 is preferably of sufficient size to allow baby foods to readily pass therethrough, but not so large as to promote spillage or leakage.

In use, the syringe 12 is filled with food or a liquid (in the latter case such as a juice or medicine, such as an antibiotic, and over-the-counter pain reliever, or the like) of a consistency that permits the food or liquid to be loaded into the inlet/outlet end 20 and controllably discharged through the inlet/outlet end 20 and into a child's mouth. Preferably, the loading process may be undertaken when the syringe 12 is assembled with the toy 14, although the syringe 12 may be loaded when the syringe 12 is disassembled from the toy 14. Also, if desired, the loading process may be undertaken through the inlet/outlet end 20 by placing the end 20 into a container holding food or liquid and withdrawing the plunger 24 while grasping the handle 58 and/or the barrel 16, as should be evident. Alternatively, food and/or liquid may be loaded through the plunger end 22 after first removing the plunger 24 from the barrel 16.

Preferably, the toy 14 is chilled or frozen prior to use so that the surfaces of the toy 14 are cooled. The child may be given the toy during and/or after feeding so that the child may teethe on and/or play with same. Preferably, although not necessarily, the syringe 12 is removed from the toy 14 before giving the child the toy 14. Alternatively, the toy 14 may be gently heated, for example, under warm water, before feeding and/or giving the toy 14 to the child.

The syringe 12 may be removed from the toy 14 and may be inserted in a corresponding recess of a different toy, if desired. Thus, a user need only have a single syringe 12. Also, the syringe 12 is preferably of a type that is readily available so that the user may obtain replacement or extra syringes.

INDUSTRIAL APPLICABILITY

In summary, using the syringe 12 for feeding keeps feeding time mess to a minimum, and allowing the child to play with the toy 14 after feeding encourages the child to teethe on the toy 14. Chilling or gently warming the toy 14 can help soothe the child, particularly when gums are sore or sensitive. The toy 14 is preferably readily washable, for example, in soapy water and/or in a dishwasher, as is the syringe 12 so that proper hygiene can be maintained.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Numerous modifications to the present disclosure will be apparent to those skilled in the art in view of the foregoing description. It should be understood that the illustrated embodiments are exemplary only, and should not be taken as limiting the scope of the disclosure.

We claim:

1. A device, comprising: a syringe; and an integral body comprising one or more of an action figure, a miniaturized version of a useful article, a fanciful version of a useful article, or a playful or fanciful other object, wherein the body includes flexible surfaces defining a recess and a slot wherein the recess and the slot extend along substantially a full length of the body between a front body end a back body end and the slot is in communication with the recess over the full length of the body and wherein the body includes a reduced diameter flange at one end of the body and an entirety of the body comprises a teething device; and wherein the syringe is separate from the body and is removably carried by the body inside the recess in abutment with both the flexible surfaces and the reduced diameter flange and wherein the syringe is exposed outside of the body by the slot over the full length of the body.

2. The device of claim 1, wherein the body comprises a flexible outer member and one or more of a liquid, a gel, and particulates disposed in the flexible outer member.

3. The device of claim 1, wherein the body comprises a flexible outer member.

4. The device of claim 3, wherein one or more of a freezable liquid and a freezable gel is disposed in the flexible outer member.

5. The device of claim 1, wherein the syringe is fixedly received within the recess.

6. The device of claim 1, wherein the syringe includes a cylindrical barrel and the recess comprises a cylindrical recess that fixedly receives the barrel.

7. The device of claim 6, wherein the syringe includes a tip at a first end and a plunger at a second end opposite the first end.

8. The device of claim 7, wherein the body comprises a flexible outer member and one or more of a liquid, a gel, and particulates disposed in the flexible outer member.

9. A device, comprising: a syringe; and an integral body comprising one or more of an action figure, a miniaturized version of a useful article, a fanciful version of a useful article, or a playful or fanciful other object, and wherein the body includes a recess extending substantially along the length of the body wherein the syringe is carried in the recess and is separate from the body; wherein the body comprises a flexible outer member extending over an entirety of the body and one or more of a freezable liquid and a freezable gel disposed in the flexible outer member wherein the entirety of the body comprises a teething device; and wherein the syringe includes a cylindrical barrel and a surface proximate an end of the syringe having a shoulder and the body includes a cylindrical recess that fixedly receives the barrel and a reduced diameter flange wherein the shoulder abuts the reduced diameter flange.

10. The device of claim 9, wherein the end of the syringe comprises a first syringe end and the syringe further includes a tip at the first end and a plunger at a second end opposite the first end.

11. The device of claim 9, wherein the body comprises particulates disposed in the flexible outer member.

* * * * *